United States Patent
Dieterle et al.

(12)
(10) Patent No.: US 6,888,024 B2
(45) Date of Patent: May 3, 2005

(54) HETEROGENEOUSLY CATALYZED PARTIAL GAS PHASE OXIDATION OF PROPENE TO ACRYLIC ACID

(75) Inventors: Martin Dieterle, Mannheim (DE); Jochen Petzoldt, Mannheim (DE); Klaus Joachim Müller-Engel, Stutensee (DE); Heiko Arnold, Nanjing (CN)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/799,754

(22) Filed: Mar. 15, 2004

(65) Prior Publication Data

US 2004/0242926 A1 Dec. 2, 2004

Related U.S. Application Data

(60) Provisional application No. 60/475,780, filed on Jun. 5, 2003.

(30) Foreign Application Priority Data

Mar. 25, 2003 (DE) .......................... 103 13 208

(51) Int. Cl.$^7$ .............................. C07C 51/16
(52) U.S. Cl. ..................................... 562/546
(58) Field of Search ........................ 562/546

(56) References Cited

U.S. PATENT DOCUMENTS 6,395,936 B1  5/2002  Arnold et al.

6,525,217 B1  2/2003  Unverricht et al.

FOREIGN PATENT DOCUMENTS

| DE | 199 48 241 | 4/2001 |
|---|---|---|
| DE | 199 48 248 | 4/2001 |
| DE | 199 48 523 | 4/2001 |
| DE | 199 55 168 | 5/2001 |
| EP | 1 106 598 | 6/2001 |
| WO | 199 10 506 | 9/2000 |
| WO | 199 27 624 | 12/2000 |
| WO | WO 01/36364 | 5/2001 |

*Primary Examiner*—Michael L. Shippen
(74) *Attorney, Agent, or Firm*—Oblon, Spivak, McClelland, Maier & Neustadt, P.C.

(57) ABSTRACT

In a process for heterogeneously catalyzed partial gas phase oxidation of propene to acrylic acid, the starting reaction gas mixture is oxidized at a propene loading of <160 l(STP)/l·h in a first reaction stage over a fixed catalyst bed 1 which is accommodated in two successive reaction zones A, B, and the acrolein-containing product gas mixture of the first reaction stage is subsequently oxidized in a second reaction stage over a fixed catalyst bed 2 which is a accommodated in two successive reaction zones C, D, the highest temperature of the reaction gas mixture within reaction zone A being above the highest temperature of the reaction gas mixture within reaction zone B and the highest temperature of the reaction gas mixture within reaction zone C being above the highest temperature of the reaction gas mixture within reaction zone D.

15 Claims, No Drawings

US 6,888,024 B2

HETEROGENEOUSLY CATALYZED PARTIAL GAS PHASE OXIDATION OF PROPENE TO ACRYLIC ACID

CROSS-REFERENCE TO RELATED APPLICATIONS

This application is a non-provisional application of provisional application Ser. No. 60/475,780, filed Jun. 5, 2003, which in turn finds basis of priority in German application Serial No. 103 13 208.2 filed Mar. 25, 2003.

The present invention relates to a process for partially oxidizing propene to acrylic acid in the gas phase under heterogeneous catalysis by conducting a starting reaction gas mixture 1 which comprises propene, molecular oxygen and at least one inert gas and contains the molecular oxygen and the propene in a molar $O_2 : C_3H_6$ ratio of $\geq 1$ in a first reaction stage over a fixed catalyst bed 1 which is arranged in two spatially successive reaction zones A, B, the temperature of reaction zone A being a temperature in the range from 290 to 380° C. and the temperature of reaction zone B likewise being a temperature in the range from 290 to 380° C., and whose active composition is at least one multimetal oxide comprising the elements Mo, Fe and Bi, in such a way that reaction zone A extends to a propene conversion of from 40 to 80 mol % and the propene conversion on single pass through the fixed catalyst bed 1 is $\geq 90$ mol % and the accompanying selectivity of acrolein formation and also of acrylic acid by-production taken together is $\geq 90$ mol %, the temperature of the product gas mixture leaving the first reaction stage is optionally reduced by cooling and molecular oxygen and/or inert gas are optionally added to the product gas mixture, and then the product gas mixture, as a starting reaction gas mixture 2 comprising acrolein, molecular oxygen and at least one inert gas and containing the molecular oxygen and the acrolein in a molar $O_2 : C_3H_4O$ ratio of $\geq 0.5$, is conducted in a second reaction stage over a fixed catalyst bed 2 which is arranged in two spatially successive reaction zones C, D, the temperature of reaction zone C being a temperature in the range from 230 to 320° C. and the temperature of reaction zone D likewise being a temperature in the range from 230 to 320° C., and whose active composition is at least one multimetal oxide comprising the elements Mo and V, in such a way that reaction zone C extends to an acrolein conversion of from 45 to 85 mol % and the acrolein conversion on single pass through the fixed catalyst bed 2 is $\geq 90$ mol % and the selectivity of acrylic acid formation assessed over all reaction zones, based on converted propene, is $\geq 80$ mol %, the sequence in time in which the reaction gas mixture flows through the reaction zones corresponding to the alphabetic sequence of the reaction zones.

Acrylic acid is an important monomer which finds use as such or in the form of its acrylic esters for obtaining polymers suitable, for example, as adhesives.

On the industrial scale, acrylic acid is prepared predominantly by heterogeneously catalyzed partial gas phase oxidation of propene (cf., for example, WO 01/36364).

In principle, the heterogeneously catalyzed partial gas phase oxidation of propene to acrylic acid proceeds in two chronologically successive steps.

In the first step, propene is oxidized to acrolein, and in the second step, the acrolein formed in the first step is oxidized to acrylic acid.

Typically, the heterogeneously catalyzed partial gas phase oxidation of propene to acrylic acid is therefore carried out at elevated temperatures in two spatially successive reaction stages, each of the two reaction stages using catalytically active multimetal oxide compositions which are tailored to the oxidation step to be catalyzed in the particular reaction stage. The multimetal oxide active compositions to be used in the first reaction stage for the step from propene to acrolein comprise the elements Mo, Fe and Bi, while the multimetal oxide active compositions to be used in the second reaction stage for the step from acrolein to acrylic acid comprise the elements Mo and V. No intermediate separation of the acrolein from the product gas mixture of the first reaction stage is normally carried out. Rather, the acrolein-containing product gas mixture of the first reaction stage, optionally after reducing its temperature by cooling, and also optionally after adding further molecular oxygen and/or inert gas, is generally used as such for the further oxidation of acrolein in the second reaction stage.

In addition to molecular oxygen and the reactants, the reaction gas mixture comprises inert gas in order to keep the reaction gas mixture outside the explosion range, among other reasons.

One objective of such a two-stage heterogeneously catalyzed partial gas phase oxidation of propene to acrylic acid is to achieve a very high yield $Y^{AA}$ of acrylic acid (this is the number of moles of propene converted to acrylic acid, based on the number of moles of propene used) on single pass of the reaction gas mixture through the two reaction stages under otherwise predefined boundary conditions.

A further objective of such a heterogeneously catalyzed partial gas phase oxidation of propene to acrylic acid is to achieve a very high space-time yield $STY^{AA}$ of acrylic acid (in a continuous procedure, this is the total amount of acrylic acid obtained per hour and unit of total volume of the fixed catalyst bed used in liters).

At a constant given yield $Y^{AA}$, the greater the hourly space velocity of propene on the fixed catalyst bed of the first reaction stage (fixed catalyst bed 1) (this refers to the amount of propene in liters at STP (=l (STP); the volume in liters which would be taken up by the appropriate amount of propene under standard conditions, i.e. at 25° C. and 1 bar) which is conducted as a constituent of the starting reaction gas mixture 1 through one liter of fixed catalyst bed 1 per hour), the higher the space-time yield.

The teachings of the documents WO 01/36364, DE-A 19927624, DE-A 19948248, DE-A 19948523, DE-A 19948241 and DE-A 19910506 are therefore directed toward significantly increasing the hourly space velocity of propene on the fixed catalyst bed of the first reaction stage at substantially constant $Y^{AA}$. This is achieved substantially by arranging both the fixed catalyst bed in the first reaction stage and the fixed catalyst bed in the second reaction stage each in two spatially successive temperature zones (reaction zones). The hourly space velocity of propene on the fixed catalyst bed 1 is then selected at $\geq 160$ l (STP)/l of fixed catalyst bed 1·h and the temperature of the second (in the flow direction of the reaction gas mixture) temperature zone in each case has to be at least 5° C. above the temperature of the first temperature zone.

In a similar manner, EP-A 1106598 also teaches a process of the high load method for the heterogeneously catalyzed partial gas phase oxidation of propene to acrylic acid, in which the fixed catalyst beds of the two reaction stages are each arranged in a plurality of temperature zones. According to the teaching of EP-A 1106598, the temperature difference of a subsequent temperature zone in the flow direction of the reaction gas mixture can be either more or less than 5° C. above the temperature of the preceding temperature zone, and EP-A 1106598 leaves completely open the question of under which conditions a larger and under which conditions a smaller temperature difference should be applied.

EP-A 1106598 also leaves completely open the question of what the temperature of a reaction zone or a temperature zone means.

In contrast, in the remaining prior art documents cited, the temperature of a reaction zone refers to the temperature of the fixed catalyst bed disposed in the reaction zone when performing the process in the absence of a chemical reaction. When this temperature within the reaction zone is not constant, the term temperature of a reaction zone refers to the (numerical) mean of the temperature of the fixed catalyst bed along the reaction zone. It is essential that the individual reaction zones are heated substantially independently of one another, so that a reaction zone always corresponds to a temperature zone. The aforementioned definition of the temperature of a reaction zone also applies in this document.

Since the heterogeneously catalyzed partial gas phase oxidation of propene to acrylic acid is a markedly exothermic reaction, the temperature of the reaction gas mixture on reactive pass through the fixed catalyst bed is generally different from the temperature of a reaction zone. It is normally above the temperature of the reaction zone and, within a reaction zone, generally passes through a maximum (heating point maximum) or falls starting from a maximum value.

However, a disadvantage of the teachings of the prior art is that they are exclusively directed toward operating a multizone arrangement under a high propene loading. This is disadvantageous in that such a procedure is inevitably accompanied by a high $STY^{AA}$. However, this assumes a corresponding market requirement for acrylic acid. When the latter is absent (for example temporarily), the multizone arrangement then necessarily has to be operated at lower propene loadings, and another target parameter which then comes to the forefront is a very high selectivity of acrylic acid formation, based on converted propene ($S^{AA}$). This is the molar amount of acrylic acid formed on single pass through the multizone arrangement, based on the number of moles of converted propene.

It is an object of the present invention to provide a process for heterogeneously catalyzed partial gas phase oxidation of propene to acrylic acid in a multizone arrangement, in which acrylic acid is formed with very high selectivity at propene loadings of <160 l (STP)/l·h.

We have found that this object is achieved by a process for partially oxidizing propene to acrylic acid in the gas phase under heterogeneous catalysis by conducting a starting reaction gas mixture 1 which comprises propene, molecular oxygen and at least one inert gas and contains the molecular oxygen and the propene in a molar $O_2$: $C_3H_6$ ratio of $\geq 1$ in a first reaction stage over a fixed catalyst bed 1 which is arranged in two spatially successive reaction zones A, B, the temperature of reaction zone A being a temperature in the range from 290 to 380° C. and the temperature of reaction zone B likewise being a temperature in the range from 290 to 380° C., and whose active composition is at least one multimetal oxide comprising the elements Mo, Fe and Bi, in such a way that reaction zone A extends to a propene conversion of from 40 to 80 mol % and the propene conversion on single pass through the fixed catalyst bed 1 is $\geq 90$ mol % and the accompanying selectivity of acrolein formation and also of acrylic acid by-production taken together is $\geq 90$ mol %, the temperature of the product gas mixture leaving the first reaction stage is optionally reduced by cooling and molecular oxygen and/or inert gas are optionally added to the product gas mixture, and then the product gas mixture, as a starting reaction gas mixture 2 comprising acrolein, molecular oxygen and at least one inert gas and containing the molecular oxygen and the acrolein in a molar $O_2$: $C_3H_4O$ ratio of $\geq 0.5$, is conducted in a second reaction stage over a fixed catalyst bed 2 which is arranged in two spatially successive reaction zones C, D, the temperature of reaction zone C being a temperature in the range from 230 to 320° C. and the temperature of reaction zone D likewise being a temperature in the range from 230 to 320° C., and whose active composition is at least one multimetal oxide comprising the elements Mo and V, in such a way that reaction zone C extends to an acrolein conversion of from 45 to 85 mol % and the acrolein conversion on single pass through the fixed catalyst bed 2 is $\geq 90$ mol % and the selectivity of acrylic acid formation assessed over all reaction zones, based on converted propene, is $\geq 80$ mol %, the sequence in time in which the reaction gas mixture flows through the reaction zones corresponding to the alphabetic sequence of the reaction zones, wherein a) the hourly space velocity of the propene contained in the starting reaction gas mixture 1 on the fixed catalyst bed 1 is <160 l (STP) of propene/l of fixed catalyst bed 1·h and $\geq 90$ l (STP) of propene/l of fixed catalyst bed 1·h;

b) the volume-specific activity of the fixed catalyst bed 1 is either constant or increases at least once in the flow direction of the reaction gas mixture over the fixed catalyst bed 1;

c) the difference $T^{maxA}-T^{maxB}$, formed from the highest temperature $T^{maxA}$ which the reaction gas mixture has within reaction zone A and the highest temperature $T^{maxB}$ which the reaction gas mixture has within reaction zone B, is $\geq 0°$ C.;

d) the hourly space velocity of the acrolein contained in the starting reaction gas mixture 2 on the fixed catalyst bed 2 is $\leq 145$ l (STP) of acrolein/l of fixed catalyst bed 2·h and $\geq 70$ l (STP) of acrolein/l of fixed catalyst bed 2·h;

e) the volume-specific activity of the fixed catalyst bed 2 increases at least once in the flow direction of the reaction gas mixture over the fixed catalyst bed 2; and f) the difference $T^{maxC}-T^{maxD}$, formed from the highest temperature $T^{maxC}$ which the reaction gas mixture has within reaction zone C and the highest temperature $T^{maxD}$ which the reaction gas mixture has within reaction zone D, is $\geq 0°$ C.

In general, the difference $T^{maxA}-T^{maxB}$ in the process according to the invention will not be more than 80° C.

According to the invention, preference is given to $T^{maxA}-T^{maxB}$ being $\geq 3°$ C. and $\leq 70°$ C. Very particular preference is given to $T^{maxA}-T^{maxB}$ in the process according to the invention being $\geq 20°$ C. and $\leq 60°$ C.

Also, the difference $T^{maxC}-T^{maxD}$ in the process according to the invention will generally not be more than 75° C.

According to the invention, preference is given to $T^{maxC}-T^{maxD}$ being $\geq 3°$ C. and $\leq 60°$ C. Very particular preference is given to $T^{maxC}-T^{maxD}$ in the process according to the invention being $\geq 5°$ C. and $\leq 40°$ C.

The process according to the invention proves advantageous, for example, when the hourly space velocity of the propene contained in the starting reaction gas mixture 1 on the fixed catalyst bed 1 is $\geq 90$ l (STP) of propene/l·h and $\leq 155$ l (STP) of propene/l·h, or $\geq 100$ l (STP) propene/l·h and $\leq 150$ l (STP) pf propene/l·h, or $\geq 110$ l (STP) of propene/l·h and $\leq 145$ l (STP) of propene/l·h, or $\geq 120$ l (STP) of propene/l·h and $\leq 140$ l (STP) of propene/l·h, or $\geq 125$ l (STP) of propene/l·h and $\leq 135$ l (STP) of propene/ l·h, and the hourly space velocity of the acrolein contained in the starting reaction gas mixture 2 on the fixed catalyst bed 2 is ≧70 l (STP) of acrolein/l·h and ≦140 l (STP) of acrolein/l·h, or ≦135 l (STP) of acrolein/l·h, or ≧80 l (STP) of acrolein/l·h and ≦130 l (STP) of acrolein/l·h, or ≧90 l (STP) of acrolein/l·h and ≦125 l (STP) of acrolein/l·h, or ≧100 l (STP) of acrolein/l·h and ≦120 l (STP) of acrolein/l·h, or ≧105 l (STP) of acrolein/l·h and ≦115 l (STP) of acrolein/l·h.

It will be appreciated that the process according to the invention can also be applied when the hourly space velocity of the propene contained in the starting reaction gas mixture 1 on the fixed catalyst bed 1 is <90 l (STP) of propene/l·h and the hourly space velocity of the acrolein contained in the starting reaction gas mixture 2 on the fixed catalyst bed 2 is <70 l (STP) of acrolein/l·h. However, the operation of a multi-zone arrangement at such low reactant loadings would hardly be economically viable.

When performing the process according to the invention, the differences $T^{maxA}-T^{maxB}$ required in accordance with the invention are normally attained when, on the one hand, both the temperature of reaction zone A and the temperature of reaction zone B are in the range from 290 to 380° C. and, on the other hand, the difference between the temperature of reaction zone B ($T_B$) and the temperature of reaction zone A ($T_A$), i.e. $T_B-T_A$, is ≦0° C. and ≧−20° C. or ≧−10° C., or ≦0° C. and ≧−5° C., or frequently ≦0° C. and ≧−3° C.

In other words, in contrast to the teaching of the prior art for high loadings, the temperature of the subsequent zone in the process according to the invention will normally be lower than the temperature in the preceding reaction zone.

This also applies to the two reaction zones of the second reaction stage.

In other words, when performing the process according to the invention, the differences $T^{maxC}-T^{maxD}$ required in accordance with the invention are normally attained when, on the one hand, both the temperature of reaction zone C and the temperature of reaction zone D are in the range from 230 to 320° C. and, on the other hand, the difference between the temperature of reaction zone D ($T_D$) and the temperature of reaction zone C ($T_C$), i.e. $T_D-T_C$, is ≦0° C. and ≧−20° C. or ≧−10° C., or ≦0° C. and ≧−5° C., or frequently ≦0° C. and ≧−3° C.

The aforementioned statement relating to the temperature difference $T_B-T_A$ also applies when the temperature of reaction zone A is within the preferred temperature range of from 305 to 365° C., or within the particularly preferred range of from 310 to 340° C.

In a corresponding manner, the aforementioned statement relating to the temperature difference $T_D-T_C$ also applies when the temperature of reaction zone C is within the preferred temperature range of from 250 to 300° C., or within the particularly preferred range of from 260° C. to 280° C.

The working pressure in both reaction stages of the process according to the invention can either be below atmospheric pressure (for example down to 0.5 bar) or above atmospheric pressure. Typically, the working pressure in the two reaction stages of the process according to the invention will be at values of from 1 to 5 bar, frequently from 1 to 3 bar. Normally, the reaction pressure will not exceed 100 bar in either of the two reaction stages.

In general, the propene conversion based on single pass of the fixed catalyst bed 1 in the process according to the invention will be ≧92 mol % or ≧94 mol %.

The selectivity of product of value formation (sum of acrolein formation and acrylic acid by-production) in the case of suitable catalyst selection in a manner known per se will regularly be ≧92 mol %, or ≧94 mol %, frequently ≧95 mol %, or ≧96 mol % or ≧97 mol %.

According to the invention, preference is given to reaction zone A extending to a propene conversion of from 50 to 70 mol % and more preferably to a propene conversion of from 60 to 70 mol %.

In general, the hourly space velocity of acrolein on the fixed catalyst bed 2 in the process according to the invention will be about 10 l (STP)/l·h, frequently about 20 to 25 l (STP)/l·h, below the hourly space velocity of propene on the fixed catalyst bed 1. This can be primarily attributed to neither the conversion of propene nor the selectivity of acrolein formation generally attaining 100%.

According to the invention, preference is given to reaction zone C extending to a conversion of the acrolein coming from the first reaction stage of from 50 to 85 mol % or from 60 to 85 mol %.

In general, the acrolein conversion based on single pass of the fixed catalyst bed 2 in the process according to the invention will be ≧92 mol % or ≧94 mol % or ≧96 mol % or ≧98 mol % and frequently even ≧99 mol % or more.

When the fixed catalyst bed 2 is selected appropriately in a manner known per se, the selectivity of acrylic acid formation assessed over both reaction stages in the process according to the invention, based on converted propene, may be at values of ≧83 mol %, frequently at ≧85 mol %, or ≧88 mol %, often at ≧90 mol %, or ≧93 mol %.

According to the invention, the molar $O_2$: $C_3H_6$ ratio in the starting reaction gas mixture 1 has to be ≧1. Typically, this ratio will be at values of ≦3. According to the invention, the molar $O_2$: $C_3H_6$ ratio in the starting reaction gas mixture 1 will frequently be ≧1.5 and ≦2.0.

According to the invention, the molar $O_2$: $C_3H_4O$ ratio in the starting reaction gas mixture 2 is preferably likewise ≧1. Typically, this ratio will likewise be at values of ≦3. According to the invention, the molar $O_2$: acrolein ratio in the starting reaction gas mixture 2 will frequently be from 1 to 2 or from 1 to 1.5.

Useful catalysts for the fixed catalyst bed 1 of the process according to the invention include all of those catalysts whose active composition is at least one multimetal oxide comprising Mo, Bi and Fe.

These are in particular the multimetal oxide active compositions of the general formula I of DE-A 19955176, the multimetal oxide active compositions of the general formula I of DE-A 19948523, the multimetal oxide active compositions of the general formulae I, II and III of DE-A 10101695, the multimetal oxide active compositions of the general formulae I, II and III of DE-A 19948248 and the multimetal oxide active compositions of the general formulae I, II and III of DE-A 19955168 and also the multimetal oxide active compositions specified in EP-A 700714.

Also suitable for the fixed catalyst bed 1 are the multimetal oxide catalysts comprising Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This applies in particular for the exemplary embodiments in these documents, and among these particular preference is given to those of EP-A 15565, EP-A 575897, DE-A 19746210 and DE-A 19855913. Particular emphasis is given in this context to a catalyst according to example 1c from EP-A 15565 and also to a catalyst to be prepared in a corresponding manner but having the active composition Mo$_{12}$Ni$_{6.5}$Zn$_2$Fe$_2$Bi$_1$P$_{0.0065}$K$_{0.06}$Ox.10 SiO$_2$. Emphasis is also given to the example having the serial number 3 from DE-A 19855913 (stoichiometry: Mo$_{12}$Co$_7$Fe$_3$Bi$_{0.6}$K$_{0.08}$Si$_{1.6}$Ox) as an unsupported hollow cylinder catalyst of geometry 5 mm×3 mm×2 mm or 5 mm×2 mm×2 mm (each external diameter×height×internal diameter) and also to the unsupported multimetal oxide II catalyst according to example 1 of DE-A 19746210. Mention should also be made of the multimetal oxide catalysts of U.S. Pat. No. 4,438,217. The latter is true in particular when these have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable are the multimetal oxide catalysts and geometries of DE-A 10101695 or WO 02/062737.

Also suitable are example 1 of DE-A 10046957 (stoichiometry:  [Bi$_2$W$_2$O$_9$×2WO$_3$]$_{0.5}$·[Mo$_{12}$Co$_{5.8}$Fe$_{2.94}$Si$_{1.59}$K$_{0.08}$O$_x$]$_1$) as an unsupported hollow cylinder (ring) catalyst of geometry 5 mm×3 mm×2 mm or 5 mm×2 mm×2 mm (each external diameter×length×internal diameter), and also the coated catalysts 1, 2 and 3 of DE-A 10063162 (stoichiometry: Mo$_{12}$Bi$_{1.0}$Fe$_3$Co$_7$Si$_{1.6}$K$_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multiplicity of the multimetal oxide active compositions suitable for the catalysts of the fixed catalyst bed 1 can be encompassed by the general formula I $$Mo_{12}Bi_aFe_bX^1_cX^2_dX^3_eX^4_fO_n \quad (I)$$

where the variables are defined as follows:
X$^1$=nickel and/or cobalt,
X$^2$=thallium, an alkali metal and/or an alkaline earth metal,
X$^3$=zinc, phosphorus, arsenic, boron, antimony, tin, cerium, lead and/or tungsten,
X$^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements other than oxygen in I.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture corresponding to their stoichiometry from suitable sources of their elemental constituents and calcining it at temperatures of from 350 to 650° C. The calcination may be effected either under inert gas or under an oxygen atmosphere, for example air (mixture of inert gas and oxygen) and also under a reducing atmosphere (for example mixture of inert gas, NH$_3$, CO and/or H$_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as NH$_4$OH, (NH$_4$)$_2$CO$_3$, NH$_4$NO$_3$, NH$_4$CHO$_2$, CH$_3$COOH, NH$_4$CH$_3$CO$_2$ and/or ammonium oxalate which decompose and/or can be decomposed on later calcining at the latest to release compounds in gaseous form can be additionally incorporated into the dry mixture).

The starting compounds for preparing the multimetal oxide active compositions I can be intimately mixed in dry or in wet form. When they are mixed in dry form, the starting compounds are advantageously used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

Typically, the multimetal oxide active compositions of the general formula I are used in the fixed catalyst bed 1 not in powder form, but rather shaped into certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined can be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is advantageously moistened and dried again after application, for example by means of hot air. The coating thickness of the powder composition applied to the support body is advantageously selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave inertly with regard to the target reaction on which the process according to the invention in the first reaction stage is based. The support bodies can have a regular or irregular shape, although preference is given to regularly shaped support bodies having distinct surface roughness, for example spheres or hollow cylinders. It is suitable to use substantially nonporous, surface-roughened spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings suitable as support bodies according to the invention, the wall thickness is also typically from 1 to 4 mm. According to the invention, annular support bodies to be used preferably have a length of from 2 to 6 mm, an external diameter of from 4 to 8 mm and a wall thickness of from 1 to 2 mm. Suitable as support bodies according to the invention are in particular rings of the geometry 7 mm×3 mm×4 mm (external diameter× length×internal diameter). It will be appreciated that the fineness of the catalytically active oxide compositions to be applied to the surface of the support body will be adapted to the desired coating thickness (cf. EP-A 714 700).

Suitable multimetal oxide active compositions for the catalysts of the first reaction stage are also compositions of the general formula II $$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad (II)$$

where the variables are defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.1 to 8,
b'=from 0.1 to 30,
c'=from 0 to 4,
d'=from 0 to 20,
e'>$\geq$0 to 20,
f'=from 0 to 6,
g'=from 0 to 15,
h'=from 8 to 16,
x',y'=numbers which are determined by the valency and frequency of the elements other than oxygen in II and
p,q=numbers whose p/q ratio is from 0.1 to 10,
comprising three-dimensional regions of the chemical composition $Y^1_{a'}Y^2_{b'}O_{x'}$ which are delimited from their local environment as a consequence of their different chemical composition from their local environment, and whose maximum diameter (longest line through the center of the region and connecting two points on the surface (interface)) is from 1 nm to 100 μm, frequently from 10 nm to 500 nm or from 1 μm to 50 or 25 μm.

Particularly advantageous multimetal oxide compositions II according to the invention are those in which $Y^1$ is only bismuth.

Among these, preference is given in turn to those of the general formula III $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \quad (III)$$

where the variables are defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h''from 0 to 1,
x'',y''=numbers which are determined by the valency and frequency of the elements other than oxygen in III,
p'',q''=numbers whose p''/q'' ratio is from 0.1 to 5, preferably from 0.5 to 2, and particular preference is given to those compositions III in which $Z^2_{b''}$=(tungsten)$_{b'}$ and $Z^2_{12}$=(molybdenum)$_{12}$.

It is also advantageous when at least 25 mol % (preferably at least 50 mol % and more preferably at least 100 mol %) of the total proportion of $[Y^1_{a'}Y^2_{b'}O_{x'}]_p$ ($[Bi_{a''}Z^2_{b''}O_{x''}]_{p''}$) of the multimetal oxide compositions II (multimetal oxide compositions II) suitable according to the invention in the multimetal oxide compositions II (multimetal oxide compositions III) suitable according to the invention are in the form of three-dimensional regions of the chemical composition $Y^1_{a'}Y^2_{b'}O_{x'}[Bi_{a''}Z^2_{b''}O_{x''}]$ which are delimited from their local environment as a consequence of their different chemical composition from their local environment, and whose maximum diameter is in the range from 1 nm to 100 μm.

With regard to the shaping, the statements made for the multimetal oxide I catalysts apply to the multimetal oxide II catalysts.

The preparation of multimetal oxide II active compositions is described, for example, in EP-A 575897 and also in DE-A 19855913.

The inert support materials recommended above are also useful, among other uses, as inert materials for diluting and/or delimiting the particular fixed catalyst bed or as its guard bed.

Useful active compositions for the catalysts of the fixed catalyst bed 2 are in principle all multimetal oxide compositions comprising Mo and V, for example those of DE-A 10046928.

A multiplicity of these, for example those of DE-A 19815281, can be encompassed by the general formula IV $$Mo_{12}V_aX^1_bX^2_cX^3_dX^4_eX^5_fX^6_gO_n \quad (IV)$$

where the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements other than oxygen in IV.

Embodiments among the active multimetal oxides IV which are preferred according to the invention are those which are encompassed by the following definitions of the variables of the general formula IV:

$X^1$=W, Nb and/or Cr,
$X^2$=Cu, Ni, Co and/or Fe,
$X^3$=Sb
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements other than oxygen in IV.

However, multimetal oxides IV which are very particularly preferred according to the invention are those of the general formula V $$Mo_{12}V_{a'}Y^1{}_{b'}Y^2{}_{c'}Y^5{}_{f'}Y^6{}_{g'}O_{n'} \qquad (V)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements other than oxygen in V.

The multimetal oxide active compositions (IV) which are suitable according to the invention are obtainable in a manner known per se, for example disclosed in DE-A 4335973 or in EP-A 714700.

In principle, multimetal oxide active compositions, in particular those of the general formula IV, suitable for the catalysts of the fixed catalyst bed 2 can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions IV include those compounds which are already oxides and/or those compounds which can be converted to oxides by heating, at least in the presence of oxygen.

The starting compounds for preparing multimetal oxide compositions IV can be intimately mixed in dry or in wet form. When they are mixed in dry form, the starting compounds are advantageously used as finely divided powder and subjected to calcining after mixing and optional compaction. However, preference is given to the intimate mixing in wet form.

This is typically done by mixing the starting compounds in the form of an aqueous solution and/or suspension. Particularly intimate dry mixtures are obtained in the mixing process described when the starting materials are exclusively sources of the elemental constituents in. dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, in particular those of the general formula IV, are generally used in the fixed catalyst bed 2 not in powder form, but rather shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinder, a wall thickness of from 1 to 3 mm is advantageous. It will be appreciated that the unsupported catalyst may also have spherical geometry and the spherical diameter may be from 2 to 10 mm.

It will be appreciated that the pulverulent active composition or its pulverulent precursor composition which is yet to be calcined can also be shaped by applying to preshaped inert catalyst supports. The coating of the support bodies to prepare the coated catalysts is generally performed in a rotatable vessel, as disclosed, for example, by DE-A 2909671, EP-A 293859 or from EP-A 714700.

To coat the support bodies, the powder composition to be applied is advantageously moistened and is dried again after application, for example by means of hot air. The coating thickness of the powder composition applied to the support body is advantageously selected within the range from 10 to 1 000 µm, preferably within the range from 50 to 500 µm and more preferably in the range from 150 to 200 µm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders having a grit layer. It is suitable to use substantially nonporous, surface-roughened, spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Advantageous multimetal oxide active compositions to be used for the catalysts of the fixed catalyst bed 2 are also compositions of the general formula VI $$[D]_p[E]_q \qquad (VI)$$

where the variables are defined as follows:

$D = Mo_{12}V_{a''}Z^1_{b''}Z^2_{c''}Z^3_{d''}Z^4_{e''}Z^5_{f''}Z^6_{g''}O_{x'''}$, $E = Z^7_{12}Cu_{h''}H_{i''}O_{y''}$, $Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements other than oxygen in VI and
p,q=numbers other than zero whose p/q ratio is from 160:1 to 1:1,
and which are obtainable by separately preforming a multimetal oxide composition E

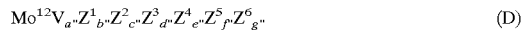
$$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the above-mentioned elements in the stoichiometry D

$$Mo^{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions VI in which the preformed solid starting composition 1 is incorporated into an aqueous starting composition 2 at a temperature of <70° C. A detailed description of the preparation of multimetal oxide VI catalysts is contained, for example, in EP-A 668104, DE-A 19736105, DE-A 10046928, DE-A 19740493 and DE-A 19528646.

With regard to the shaping, the statements made for the multimetal oxide IV catalysts apply to the multimetal oxide VI catalysts.

Further suitable multimetal oxide compositions for the catalysts of the fixed catalyst bed 2 are those of DE-A 19815281, in particular all exemplary embodiments from this document. With regard to the shaping, the same applies as was stated above.

For the fixed catalyst bed 2 of the process according to the invention, particularly suitable catalysts are the coated catalysts S1 (stoichiometry: $Mo_{12}V_3W_{1.2}Cu_{2.4}O_n$) and S7 (stoichiometry: $Mo_{12}V_3W_{1.2}Cu_{1.6}Ni_{0.8}O_n$) from DE-A 4442346 having an active composition fraction of 27% by weight and a coating thickness of 230 μm, the coated catalyst from preparative example 5 of DE-A 10046928 (stoichiometry: $Mo_{12}V_3W_{1.2}Cu_{2.4}O_n$) having an active composition fraction of 20% by weight, to coated catalysts of examples 1 to 5 from DE-A 19815281, but equally the abovementioned coated catalysts for the second reaction stage applied to support rings of geometry 7 mm×3 mm×4 mm (external diameter×length×internal diameter) having an active composition fraction of 20% by weight (based on the overall composition of the coated catalyst), and also a coated catalyst having a biphasic active composition of stoichiometry $(Mo_{10.4}V_3W_{1.2}O_x)$ $(CuMo_{0.5}W_{0.5}O_4)_{1.6}$ and prepared according to DE-A 19736105 and having an active composition fraction of 20% by weight applied to the abovementioned 7 mm×3 mm×4 mm support.

The catalysts recommended above for the second reaction stage are only suitable for the two reaction stages when everything is retained except the support geometry which is changed to 5 mm×3 mm×1.5 mm (external diameter× length×internal diameter). The multimetal oxides mentioned can also be used in the second reaction stage in the form of the corresponding unsupported catalyst rings.

To prepare the fixed catalyst bed 1 in the process according to the invention, it is possible to use only the shaped catalyst bodies having the appropriate multimetal oxide active composition or else substantially homogeneous mixtures of shaped catalyst bodies having multimetal oxide active composition and shaped bodies (shaped diluent bodies) behaving substantially inertly with regard to the heterogeneously catalyzed partial gas phase oxidation and having no multimetal oxide active composition. Useful materials for such inert shaped bodies include in principle all of those which are also suitable as support material for coated catalysts suitable in accordance with the invention. Useful such materials include, for example, porous and nonporous aluminum oxides, silicon dioxide, thorium dioxide, zirconium dioxide, silicon carbide, silicates such as magnesium silicate or aluminum silicate or the steatite already mentioned (e.g. Steatite C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted by them (the above statements also apply in the same way to the substantially homogeneous mixtures of shaped catalyst bodies having appropriate multimetal oxide active composition and shaped diluent bodies which can be used to provide the fixed catalyst bed 2).

According to the invention, it is advantageous when the chemical composition of the active composition used does not change over the fixed catalyst bed 1. In other words, although the active composition used for an individual shaped catalyst body can be a mixture of different multimetal oxides containing the elements Mo, Fe and Bi, the same mixture then has to be used for all shaped catalyst bodies of the fixed catalyst bed 1.

In this case, the volume-specific (i.e. normalized to the unit of the volume) activity can be reduced in a simple manner, for example, by homogeneously diluting a basic amount of shaped catalyst bodies prepared in a uniform manner with shaped diluent bodies. The higher the proportion of shaped diluent bodies selected, the less active composition and catalyst activity present in a certain volume of the bed.

A volume-specific activity increasing at least once in the flow direction of the reaction gas mixture over the fixed catalyst bed 1 can therefore be attained for the process according to the invention in a simple manner, for example, by beginning the bed with a high proportion of inert shaped diluent bodies based on one type of shaped catalyst bodies, and then, either continuously or at least once or more than once abruptly (for example stepwise), reducing this proportion of shaped diluent bodies in the flow direction. When the proportion of shaped diluent bodies is left constant or no shaped diluent bodies at all are used in the fixed catalyst bed 1, this then results in a constant volume-specific activity in the flow direction of the reaction gas mixture over the fixed catalyst bed 1. However, an increase in the volume-specific activity is also possible, for example, at a constant geometry and active composition type of a shaped coated catalyst body, increasing the thickness of the active composition layer applied to this support, or, in a mixture of coated catalysts having the same geometry but having different proportions by weight of the active composition, increasing the proportion of shaped catalyst bodies having the higher proportion by weight of active composition. Alternatively, the active compositions themselves can also be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in mixtures of unsupported catalysts and of coated catalysts (having identical active composition) by varying the mixing ratio in an appropriate manner. It will be appreciated that the variants described can also be used in combination.

It is of course also possible to use mixtures of catalysts having chemically different active compositions and, as a consequence of this different composition, having different activity for the fixed catalyst bed 1. These mixtures may in turn be diluted with inert shaped diluent bodies.

Normally, the volume-specific activity in the process according to the invention will decrease not once either within the fixed catalyst bed 1 or within the fixed catalyst bed 2 in the flow direction of the reaction gas mixture.

Upstream and/or downstream of the fixed catalyst bed 1 may be disposed beds consisting exclusively of inert material (for example only shaped diluent bodies) (in this document, they are not included for terminology purposes in the fixed catalyst bed 1, since they contain no shaped bodies which have multimetal oxide active composition). The shaped diluent bodies used for the inert bed can have the same geometry as the shaped catalyst bodies used in the fixed catalyst bed 1. However, the geometry of the shaped diluent bodies used for the inert bed can also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4–5 mm.

According to the invention, preference is given in the process according to the invention to the fixed catalyst bed 1 being structured in the flow direction of the reaction gas mixture as follows.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed catalyst bed 1, a homogeneous mixture of shaped catalyst bodies and shaped diluent bodies (both preferably having substantially the same geometry), in which the proportion by weight of shaped diluent bodies (the densities of shaped catalyst bodies and of shaped diluent bodies generally differ only slightly) is normally from 5 to 40% by weight, or from 10 to 40% by weight, or from 20 to 40% by weight, or from 25 to 35% by weight. According to the invention, this first zone of the fixed catalyst bed 1 is advantageously followed to the end of the length of the fixed catalyst bed 1 (i.e., for example, to a length of from 2.00 to 3.00 m, preferably from 2.50 to 3.00 m) either by a bed of shaped catalyst bodies diluted only to a slighter extent (than in the first zone), or, most preferably, an unaccompanied (undiluted) bed of the same shaped catalyst bodies which have also been used in the first zone. The aforementioned applies in particular when the shaped catalyst bodies used in the fixed catalyst bed 1 are unsupported catalyst rings or coated catalyst rings (in particular those which are listed in this document as preferred). For the purposes of the aforementioned structuring, both the shaped catalyst bodies and the shaped diluent bodies in the process according to the invention substantially have the ring geometry 5 mm×3 mm×2 mm (external diameter×length×internal diameter).

In a corresponding manner to that in which the volume-specific activity of the fixed catalyst bed 1 can be varied, the volume-specific activity of the fixed catalyst bed 2 can also be varied. Upstream and/or downstream of the actual fixed catalyst bed 2 may again be disposed an appropriate inert bed. However, a constant volume-specific activity within the fixed catalyst bed 2 (as is possible in accordance with the invention within the fixed catalyst bed 1) is ruled out in the process according to the invention.

Preference is given in accordance with the invention to the fixed catalyst bed 2 in the process according to the invention being structured as follows in the flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed bed catalyst bed 2, a homogeneous mixture or two (having decreasing dilution) successive homogeneous mixtures of shaped catalyst bodies and shaped diluent bodies (both preferably having substantially the same geometry), in which the proportion by weight of shaped diluent bodies (the densities of shaped catalyst bodies and of shaped diluent bodies generally differ only slightly) is normally from 10 to 50% by weight, preferably from 20 to 45% by weight and more preferably from 25 to 35% by weight. According to the invention, this first zone of fixed catalyst bed 2 is then advantageously followed to the end of the length of the fixed catalyst bed 2 (i.e., for example, to a length of from 2.00 to 3.00 m, preferably from 2.50 to 3.00 m) by either a bed of the shaped catalyst bodies diluted only to a slighter extent (than in the first zone) or, most preferably, an unaccompanied bed of the same shaped catalyst bodies which have also been used in the first zone.

The aforementioned applies in particular when the shaped catalyst bodies used in the fixed catalyst bed 2 are coated catalyst rings or coated catalyst spheres (in particular those which are listed in this document as preferred). For the purposes of the aforementioned structuring, both the shaped catalyst bodies or their support rings and the shaped diluent bodies in the process according to the invention substantially have the annular geometry 7 mm×3 mm×4 mm (external diameter×length×internal diameter).

The abovementioned also applies when, instead of inert shaped diluent bodies, shaped coated catalyst bodies are used as active composition content is from 2 to 15% by weight lower than the active composition content of the shaped coated catalyst bodies at the end of the fixed catalyst bed 2.

In an advantageous manner from an application point of view, the first reaction stage of the process according to the invention is carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3147084, DE-A 2201528, EP-A 383224 and DE-A 2903218 are also suitable for carrying out the first reaction stage of the process according to the invention.

In other words, in the simplest manner, the fixed catalyst bed 1 to be used in accordance with the invention (possibly with downstream and/or upstream inert beds) is disposed in the metal tubes of a tube bundle reactor and two spatially separated heating media, generally salt melts, are conducted around the metal tubes. The tube section over which the particular salt bath extends represents a reaction zone in accordance with the invention. In other words, in the simplest manner, for example, a salt bath A flows around that section of the tubes (reaction zone A) in which propene is oxidatively converted (on single pass) until a conversion in the range from 40 to 80 mol % is achieved, and a salt bath B flows around the section of the tubes (reaction zone B) in which the propene is subsequently oxidatively converted (on single pass) until a conversion value of at least 90 mol % is achieved (if required, the reaction zones A, B to be used in accordance with the invention can be followed by further reaction zones which are maintained at individual temperatures).

It is advantageous from an application point of view if the first reaction stage of the process according to the invention includes no further reaction zones. In other words, the salt bath B advantageously flows around the section of the tubes in which propene is subsequently oxidatively converted (on single pass) up to a conversion value of $\geq 90$ mol %, or $\geq 92$ mol %, of $\geq 94$ mol % or more.

Typically, the beginning of the temperature zone B lies beyond the heating point maximum of temperature zone A.

According to the invention, both salt baths A, B can be conducted in cocurrent or in countercurrent through the space surrounding the reaction tubes relative to the flow direction of the reaction gas mixture flowing through the reaction tubes. It will be appreciated that, in accordance with the invention, cocurrent flow may be applied in reaction zone A and countercurrent flow in reaction zone B (or vice versa).

In all of the aforementioned cases, it will be appreciated that a transverse flow can be superimposed on the parallel flow of the salt melt relative to the reaction tubes taking place within the particular reaction zone, so that the individual reaction zone corresponds to a tube bundle reactor as described in EP-A 700714 or in EP-A 700893, which results overall in a meandering flow profile of the heat exchange medium in a longitudinal section through the catalyst tube bundle.

Advantageously, the starting reaction gas mixture 1 in the process according to the invention is fed to the fixed catalyst bed 1 preheated to the reaction temperature.

Typically, the catalyst tubes in the two-zone tube bundle reactors are manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each temperature zone, the fixed catalyst bed 1 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (the catalyst tube pitch) is from 35 to 45 mm (cf., for example, EP-B 468290).

Useful heat exchange media for the two-zone method are also in particular fluid heating media. It is particularly advantageous to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate within the two heat exchange medium circuits required is selected in such a way that the temperature of the heat exchange medium rises from the entrance into the reaction zone to the exit from the reaction zone (as a result of the exothermicity of the reaction) by from 0 to 15° C. In other words, the aforementioned ΔT may be from 1 to 10° C., or from 2 to 8° C., or from 3 to 6° C., in accordance with the invention.

According to the invention, the entrance temperature of the heat exchange medium into reaction zone A is normally in the range from 290 to 380° C., preferably in the range from 305 to 365° C. and more preferably in the range from 310 to 340° C. or is 330° C. According to the invention, the entrance temperature of the heat exchange medium into reaction zone B is normally likewise in the range from 290 to 380° C., but at the same time normally from $\geq 0°$ C. to $\leq 20°$ C. or $\leq 10°$ C., or $\geq 0°$ C. and $\leq 5°$ C., or frequently $\geq 0°$ C. and $\leq 3°$ C., below the entrance temperature of the heat exchange medium entering reaction zone A.

It is pointed out once again at this juncture that, for an implementation of reaction stage 1 of the process according to the invention, it is possible to use in particular the two-zone tube bundle reactor type described in DE-B 2201528 which includes the possibility of removing the hotter heat exchange medium of reaction zone B to reaction zone A, in order to optionally heat a cold starting reaction gas mixture or a cold cycle gas. The tube bundle characteristics within an individual reaction zone may also be configured as described in EP-A 382098.

It has proven advantageous in accordance with the invention to cool the product gas mixture leaving the first reaction stage before entering into the second reaction stage in a direct and/or indirect manner, in order to suppress subsequent full combustion of portions of the acrolein formed in the first reaction stage. To this end, an aftercooler is arranged between the two reaction stages. In the simplest case, this may be an indirect tube bundle heat exchanger. In this case, the product gas mixture is generally conducted through the tubes and a heat exchange medium is conducted around the tubes and may be of the type corresponding to the heat exchange media recommended for the tube bundle reactors. Advantageously, the tube interior is filled with inert random packings (for example spirals of stainless steel, rings of steatite, spheres of steatite, etc.). These improve the heat exchange and capture any molybdenum trioxide subliming from the fixed catalyst bed of the first reaction stage before its entry into the second reaction stage. It is advantageous if the aftercooler is manufactured from stainless steel coated with zinc silicate primer.

In general, the propene conversion based on single pass in the first reaction stage of the process according to the invention will be ≧92 mol % or ≧94 mol %. According to the invention, the resulting selectivity in the first reaction stage of acrolein formation and also of acrylic acid by-production together on single pass will regularly be ≧92 mol % or ≧94 mol %, frequently ≧95 mol % or ≧96 mol % or ≧97 mol %.

Useful sources for the molecular oxygen required in the first reaction stage include both air and air depleted of molecular nitrogen (for example, ≧90 by volume of $O_2$, ≦10% by volume of $N_2$).

It is advantageous from an application point of view to cool the product gas mixture of the first reaction stage in the aftercooler already mentioned to a temperature of from 210 to 290° C., frequently from 230 to 280° C. or from 250 to 270° C. The product gas mixture of the first reaction stage can quite possibly be cooled to temperatures which are below the temperature of the second reaction stage. However, the aftercooling described is no way obligatory and can generally be dispensed with, especially when the path of the product gas mixture from the first reaction stage to the second reaction stage is kept short. Typically, the process according to the invention is also realized in such a way that the oxygen requirement in the second reaction stage is not already covered by an appropriately high oxygen content of the starting reaction gas mixture 1, but rather that the required oxygen is added in the region between the first and second reaction stages ("secondary gas addition"). This can be before, during, after and/or for aftercooling. Useful sources for the molecular oxygen required in the second reaction stage include both pure oxygen and mixtures of oxygen and inert gas, for example air or air depleted of molecular nitrogen (for example, ≧90% by volume of $O_2$, ≦10% by volume of $N_2$). The oxygen source is regularly added compressed to the reaction pressure. It will be appreciated that the oxygen requirement in the second reaction stage of the process according to the invention can be covered by an appropriately high oxygen requirement in the first reaction stage. If required, an inert diluent gas can of course also be added as a secondary gas.

Like the implementation of the first reaction stage, the second reaction stage of the process according to the invention is also implemented in an advantageous manner from an application point of view in a two-zone tube bundle reactor, as already described for the first reaction stage. The remarks regarding two-zone tube bundle reactor for the first reaction stage therefore also apply to the two-zone tube bundle reactor for the second reaction stage.

In other words, the fixed catalyst bed 2 (including any inert beds) to be used in accordance with the invention is disposed in a simple manner in the metal tubes of a tube bundle reactor and two substantially spatially separated heating media, generally salt melts, are conducted around the metal tubes. According to the invention, the tube section over which the respective salt bath extends represents a reaction zone.

In other words, for example, a salt bath C flows around those sections of the tubes (reaction zone C) in which the acrolein is oxidatively converted (on single pass) until a conversion value in the range from 45 to 85 mol % (preferably from 50 to 85 mol %, more preferably from 60 to 85 mol %) is achieved, and a salt bath D flows around the section of the tubes (reaction zone D) in which the acrolein is subsequently oxidatively converted (on single pass) until a conversion value of at least 90 mol % is achieved (if required, the reaction zones C, D to be used in accordance with the invention can be followed by further reaction zones which are maintained at individual temperatures).

It is advantageous in accordance with the invention if the reaction stage 2 of the process according to the invention includes no further reaction zones. In other words, the salt bath D advantageously flows around the section of the tubes in which the acrolein is subsequently oxidatively converted (on single pass) to a conversion value of ≧92 mol %, or ≧94 mol % or ≧96 mol % or ≧98 mol % and frequently even ≧99 mol % or more.

Typically, the beginning of the reaction zone D lies beyond the heating point maximum of reaction zone C.

According to the invention, both salt baths C, D can be conducted in cocurrent or in countercurrent through the space surrounding the reaction tubes relative to the flow direction of the reaction gas mixture flowing through the reaction tubes. It will be appreciated that, in accordance with the invention, cocurrent flow may be applied in reaction zone C and countercurrent flow in reaction zone D (or vice versa).

In all of the aforementioned cases, it will be appreciated that a transverse flow can be superimposed on the parallel flow of the salt melt relative to the reaction tubes taking place within the particular reaction zone, so that the individual reaction zone corresponds to a tube bundle reactor as described in EP-A 700714 or in EP-A 700893, which results overall in a meandering flow profile of the heat exchange medium in a longitudinal section through the catalyst tube bundle.

Typically, the catalyst tubes in the aforementioned two-zone bundle reactors for the second reaction stage are manufactured from ferritic steel and typically have a wall thickness of from 1 to 3 mm. Their internal diameter is generally from 20 to 30 mm, frequently from 21 to 26 mm. Their length is advantageously from 3 to 4 m, preferably 3.5 m. In each temperature zone, the fixed catalyst bed 2 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (the catalyst tube pitch) is from 35 to 45 mm (cf. EP-B 468290).

Useful heat exchange media are in particular fluid heating media. It is particularly advantageous to use melts of salts such as potassium nitrate, potassium nitrite, sodium nitrite and/or sodium nitrate, or of low-melting metals such as sodium, mercury and also alloys of different metals.

In general, in all of the abovementioned flow arrangements in the two-zone tube bundle reactors of the second reaction stage, the flow rate within the two heat exchange medium circuits required is selected in such a way that the temperature of the heat exchange medium rises from the entrance into the reaction zone to the exit from the reaction zone by from 0 to 15° C. In other words, the aforementioned ΔT may be from 1 to 10° C., or from 2 to 8° C., or from 3 to 6° C., in accordance with the invention.

According to the invention, the entrance temperature of the heat exchange medium into reaction zone C is normally in the range from 230 to 320° C., preferably in the range from 250 to 300° C. and more preferably in the range from 260 to 280° C. According to the invention, the entrance temperature of the heat exchange medium into reaction zone D is normally likewise in the range from 230 to 280° C., but at the same time normally from $\geq 0°$ C. to $\leq 20°$ C. or $\leq 10°$ C., or $\geq 0°$ C. and $\leq 5°$ C., or frequently $\geq 0°$ C. and $\leq 3°$ C., below the entrance temperature of the heat exchange medium entering reaction zone C.

It is pointed out once again at this juncture that, for an implementation of the second reaction stage of the process according to the invention, it is possible to use in particular the two-zone tube bundle reactor type described in DE-B 2201528 which includes the possibility of removing the hotter heat exchange medium of reaction zone D to reaction zone C, in order to optionally heat a cold starting reaction gas mixture 2 or a cold cycle gas. The tube bundle characteristics within an individual reaction zone may also be configured as described in EP-A 382098.

It will be appreciated that the process according to the invention can also be carried out by combining two two-zone tube bundle reactors to give a four-zone tube bundle reactor, as described in WO 01/36364. In these cases, there is normally an inert bed between the fixed catalyst bed 1 and the fixed catalyst bed 2. However, such an intermediate inert bed may also be dispensed with. The length of the reaction tubes in the event of combination corresponds in many cases to the sum of the lengths of the uncombined tube bundle reactors.

The propene content in the starting reaction gas mixture 1 in the process according to the invention can, for example, be at values of from 4 to 15% by volume, frequently from 5 to 12% by volume, or from 5 to 8% by volume (based in each case on the total volume).

Frequently, the process according to the invention will be carried out at a propene:oxygen:inert gases (including steam) volume ratio in the starting reaction gas mixture 1 of 1:(1.0 to 3.0):(5 to 25), preferably 1:(1.7 to 2.3):(10 to 15). In general, at least 20% of the volume of the inert gas will consist of molecular nitrogen. However, $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of the inert gas may consist of molecular nitrogen (in this document, inert diluent gases generally refer to those of which less than 5%, preferably less than 2%, is converted in single pass through the particular reaction stage; in addition to molecular nitrogen, these are, for example, gases such as propane, ethane, methane, pentane, butane, $CO_2$, CO, steam and/or noble gases). Up to 50 mol % or up to 75 mol % and more of the inert diluent gas in the process according to the invention can consist of propane. Cycle gas, as remains after the removal of the acrylic acid from the product gas mixture, can also be a constituent of the diluent gas.

The aforementioned composition ranges are applied both in cases of secondary gas feed and in cases where no secondary gas is fed.

The starting reaction gas mixtures 1 which are advantageous according to the invention are, for example, those which are composed of from 6 to 15 (preferably from 7 to 11) % by volume of propene, from 4 to 20 (preferably from 6 to 12) % by volume of water, from $\geq 0$ to 10 (preferably from $\geq 0$ to 5) % by volume of constituents other than propene, water, oxygen and nitrogen, sufficient molar oxygen that the molar ratio of molar oxygen present to propene present is from 1.5 to 2.5 (preferably from 1.6 to 2.2), and the remainder up to 100% by volume of the total amount of molecular nitrogen, as recommended by DE-A 10302715.

According to the invention, the acrolein content in the starting reaction gas mixture 2 can have, for example, values of from 3 to 15% by volume, frequently from 4 to 10% by volume or from 5 to 8% by volume (based in each case on the total volume).

Frequently, the process according to the invention will be performed at an acrolein:oxygen:steam:inert gas volume ratio (l (STP)) present in the starting reaction gas mixture 2 of 1:(1 to 3):(0 to 20):(3 to 30), preferably of 1:(1 to 3):(0.5 to 10):(7 to 10).

It will be appreciated that the process according to the invention can also be carried out at an acrolein:oxygen:steam:others volume ratio (l (STP)) of 1:(0.9 to 1.3):(2.5 to 3.5):(10 to 12).

It is emphasized at this juncture that the multimetal oxide compositions of DE-A 10261186 are advantageous active compositions both for the fixed bed catalyst 1 and for the fixed catalyst bed 2.

Designs of a two-zone tube bundle reactor for the first reaction stage which are advantageous in accordance with the invention can have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

Catalyst tubes:
material of the catalyst tubes: ferritic steel;
dimensions of the catalyst tubes: length, for example, 3 500 mm; external diameter, for example, 30 mm; wall thickness, for example, 2 mm;
number of catalyst tubes in the tube bundle: for example, 30 000, or 28 000, or 32 000, or 34 000; in addition up to 10 thermal tubes (as described in EP-A 873 783 and EP-A 12 70 065) which are charged in the same way as the catalyst tubes (in a spiral manner rotating from the very outside toward the inside), for example of the same length and wall thickness but having an external diameter of, for example, 33.4 mm and a centered thermowell of external diameter of, for example, 8 mm and wall thickness of, for example, 1 mm;
reactor (same material as the catalyst tubes):
cylindrical vessel of internal diameter 6 000–8 000 mm;
reactor hoods plated with stainless steel of the type 1.4541; plating thickness: a few mm;
annularly arranged tube bundle, for example with free central space: diameter of the free central space: for example, 1 000–2 500 mm (for example 1 200 mm, or 1 400 mm, or 1 600 mm, or 1 800 mm, or 2 000 mm, or 2 200 mm, or 2 400 mm);
normally homogeneous catalyst tube distribution in the tube bundle (6 equidistant adjacent tubes per catalyst tube), arrangement in an equilateral triangle, catalyst tube pitch (separation of the central internal axes of immediately adjacent catalyst tubes): 35–45 mm, for example 36 mm, or 38 mm, or 40 mm, or 42 mm, or 44 mm;
the catalyst tubes are secured and sealed by their ends in catalyst tube plates (upper plate and lower plate each having a thickness, for example, of 100–200 mm) and open at their upper ends into a hood joined to the vessel which has an inlet for the starting reaction gas mixture; a separating plate of thickness 20–100 mm disposed, for example, at half the catalyst tube length, divides the reactor space symmetrically into two reaction zones (temperature zones) A (upper zone) and B (lower zone); each reaction zone is divided into 2 equidistant longitudinal sections by deflecting plates;

the deflecting plate preferably has annular geometry; the catalyst tubes are advantageously secured and sealed at the separating plate; they are not secured and sealed at the deflecting plates, so that the transverse flow rate of the salt melt within one zone is very constant;

each zone is provided with salt melt as a heat carrier by its own salt pump; the feed of the salt melt is, for example, below the deflecting plate and the withdrawal is, for example, above the deflecting plate;

a substream is, for example, removed from both salt melt circuits and cooled, for example, in one common or two separate indirect heat exchangers (steam generation);

in the first case, the cooled salt melt stream is divided, combined with the particular residual stream and pressurized into the reactor by the particular pump into the appropriate annular channel which divides the salt melt over the circumference of the vessel;

the salt melt reaches the tube bundle through the window disposed in the reactor jacket; the flow is, for example, in a radial direction to the tube bundle;

in each zone, the salt melt flows around the catalyst tubes as dictated by the deflection plate, for example in the sequence from the outside inward,
from the inside outward;

the salt melt flows through a window mounted around the circumference of the vessel and collects at the end of each zone in an annular channel disposed around the reactor jacket, in order to be pumped in a circuit including substream cooling;

the salt melt is conducted from bottom to top through each temperature zone.

The reaction gas mixture leaves the reactor of the first stage at a temperature a few degrees higher than the salt bath entrance temperature of the first reactor. For further processing, the reaction gas mixture is advantageously cooled to from 220° C. to 280° C., preferably from 240° C. to 260° C., in a separate aftercooler which is connected downstream of the reactor of the first stage.

The aftercooler is generally flanged on below the lower tube plate and normally consists of tubes of ferritic steel. Stainless steel sheet metal spirals which may be partly or fully wound are advantageously introduced into the interior of the tubes of the aftercooler, in order to improve the heat transfer.

Salt Melt:

The salt melt used may be a mixture of 53% by weight of potassium nitrate, 40% by weight of sodium nitrite and 7% by weight of sodium nitrate; both reaction zones and the aftercooler advantageously use a salt melt of the same composition; the amount of salt pumped by circulation in the reaction zones may be approx. 10 000 m³/h per zone.

Flow Control:

The starting reaction gas mixture 1 advantageously flows from top to bottom through the first stage reactor, while the salt melts having different temperatures of the individual zones are advantageously conveyed from bottom to top;

Catalyst tube and thermal tube charge (from top to bottom), for example:

Section 1: length 50 cm steatite rings of geometry 7 mm×7 mm×4 mm (external diameter×length×internal diameter) as a preliminary bed.

Section 2: length 140 cm catalyst charge of a homogeneous mixture of 30% by weight of steatite rings of geometry 5 mm×3 mm×2 mm (external diameter×length×internal diameter) and 70% by weight of unsupported catalyst from section 3.

Section 3: length 160 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2\ WO_3]_{0.5}$ $[Mo_{12}Co_{5.5}Fe_{2.94}Si_{1.59}K_{0.08}O_x]_1$).

Configurations of a two-zone tube bundle reactor for the second reaction stage which are advantageous in accordance with the invention can be designed as follows:

Everything as in the two-zone tube bundle reactor for the first reaction stage. However, the thickness of the upper and lower catalyst tube plates is frequently 100–200 mm, for example 110 mm, or 130 mm, or 150 mm, or 170 mm, or 190 mm.

The aftercooler is dispensed with; instead, the lower openings of the catalyst tubes open into a hood which is connected to the vessel at the lower end and has an outlet for the product gas mixture; the upper reaction zone is zone C and the lower reaction zone is zone D. Between the outlet "aftercooler" and the inlet "reactor for the second reaction stage" is advantageously a means for feeding compressed air.

The catalyst tube and thermal tube charge (from top to bottom) can, for example, be as follows:

Section 1: length 20 cm steatite rings of geometry 7 mm×7 mm×4 mm (external diameter×length×internal diameter) as a preliminary bed.

Section 2: length 90 cm catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

Alternatively, the first stage catalyst tube and thermal tube charge can also have the following appearance (from top to bottom):

Section 1: length 50 cm steatite rings of geometry 7 mm×7 mm×4 mm (external diameter×length×internal diameter) as a preliminary bed.

Section 2: length 300 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2WO_3]_{0.5}$. $[Mo_{12}Co_{5.6}Fe_{2.94}Si_{1.59}K_{0.08}O_x]_1$).

The second stage catalyst tube and thermal tube charge can also have the following appearance (from top to bottom):

Section 1: length 20 cm steatite rings of geometry 7 mm×7 mm×4 mm (external diameter×length×internal diameter) as a preliminary bed.

Section 2: length 140 cm catalyst charge of a homogeneous mixture of 25% by weight of steatite rings of geometry 7 mm×3 mm×4 mm (external diameter×length×internal diameter) and 75% by weight of coated catalyst from section 3.

Section 3: length 190 cm catalyst charge of annular (7 mm×3 mm×4 mm=external diameter×length×internal diameter)

coated catalyst according to preparative example 5 of DE-A 10046928 (stoichiometry: $Mo_{12}V_3W_{1.2}Cu_{2.4}O_x$).

In all of the first stage charges mentioned, the unsupported catalyst from example 1 of DE-A 10046957 can also be replaced by:
a) a catalyst according to example 1c of EP-A 15565 or a catalyst to be prepared in accordance with this example, except having the active composition $Mo_{12}Ni_{6.5}Zn_2Fe_2Bi_1P_{0.0065}K_{0.06}O_x \cdot 10\ SiO_2$;
b) example No. 3 of DE-A 19855913 as an unsupported hollow cylinder catalyst of the geometry 5 mm×3 mm×2 mm or 5 mm×2 mm×2 mm;
c) unsupported multimetal oxide II catalyst according to example 1 of DE-A 19746210;
d) one of the coated catalysts 1, 2 and 3 of DE-A 10063162, except applied in the same coating thickness to support rings of geometry 5 mm×3 mm×1.5 mm or 7 mm×3 mm×1.5 mm.

In all of the abovementioned second stage charges, the coated catalyst can be replaced in accordance with preparative example 5 of DE-A 10046928:
a) coated catalyst S1 or S7 from DE-A 4442346 having an active composition content of 27% by weight and a coating thickness of 230 µm;
b) a coated catalyst according to examples 1 to 5 of DE 19815281, except applied to support rings of geometry 7 mm×3 mm×4 mm having an active composition content of 20% by weight;
c) coated catalyst having biphasic active composition of stoichiometry $(Mo_{10.4}V_3W_{1.2}O_x)\ (CuMo_{0.5}W_{0.5}O_4)_{1.6}$, prepared according to DE-A 19736105 and having an active composition content of 20% by weight, applied to the abovementioned 7 mm×3 mm×4 mm support.

According to the invention, the fixed catalyst bed 1 and the fixed catalyst bed 2 are advantageously otherwise selected in such a way (for example by dilution with, for example, inert material) that the temperature difference between the heating point maximum of the reaction gas mixture in the individual reaction zones and the particular temperature of the reaction zone generally does not exceed 80° C. This temperature difference is usually ≦70° C., frequently from 20 to 70° C., and this temperature difference is preferably small. For safety reasons, the fixed catalyst beds 1 and 2 are also selected in a manner known per se to those skilled in the art (for example one dilution with, for example, inert material) in such a way that the peak-to-salt-temperature sensitivity as defined in EP-A 1106598 is ≦9° C., or ≦7° C., or ≦5° C., or ≦3° C.

Aftercooler and reactor for the second stage are connected by a connecting tube whose length is less than 25 m.

The reactor arrangement described and all other reactor arrangements and charges with fixed bed catalyst described in this document can also be operated at high propene loadings, as described in the documents WO 01/36364, DE-A 19927624, DE-A 19948248, DE-A 19948523, DE-A 19948241, DE-A 19910506, DE-A 10302715 and EP-A 1106598.

In this case, preference is given to the reaction zones A, B, C, D having the temperatures recommended in this document, except that the second reaction zone in each case, in accordance with the teaching of the abovementioned documents, has a higher temperature than the first reaction zone in each case. The heating point temperature in the second reaction zone in each case is always below that of the first reaction zone in each case.

However, at the propene loadings according to the invention, in the procedure according to the invention results in an increased selectivity of acrylic acid formation relative to the procedure recommended for high propene loadings.

Generally, the volume-specific activity between two fixed catalyst bed zones of a reaction stage can be experimentally differentiated in such a way that the same propene- or acrolein-containing starting reaction gas mixture is conducted under identical boundary conditions (preferably the conditions of the contemplated process) over fixed catalyst beds of the same length, but each corresponding to the composition of the particular fixed catalyst bed zone. The larger amount of propene or acrolein converted indicates the higher volume-specific activity.

In the examples and comparative examples which follow and also in the reactor arrangement above, the annular shaped diluent bodies and the annular shaped catalyst bodies in the second reaction stage can also be replaced by spherical shaped diluent bodies and spherical shaped catalyst bodies (each having radius from 2 to 5 mm and having an active composition content of from 10 to 30% by weight, frequently from 10 to 20% by weight). The statement relating to operation at high propene loadings in the above documents retain their validity.

EXAMPLE AND COMPARATIVE EXAMPLES a) Experimental Arrangement

First Reaction stage:

A reaction tube (V2A steel; external diameter 30 mm, wall thickness 2 mm, internal diameter 26 mm, length: 350 cm, and also a thermal tube (external diameter 4 mm) centered in the middle of the reaction tube to receive a thermal element which can be used to determine the temperature in the reaction tube over its entire length) is charged from top to bottom as follows:

Section 1: length 50 cm steatite rings of geometry 7 mm×7 mm×4 mm (external diameter×length×internal diameter) as a preliminary bed.

Section 2: length 140 cm catalyst charge of a homogeneous mixture of 30% by weight of steatite rings of geometry 5 mm×3 mm×2 mm (external diameter×length×internal diameter) and 70% by weight of unsupported catalyst from section 3.

Section 3: length 160 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2\ WO_3]_{0.5}$ $[Mo_{12}Co_{5.5}Fe_{2.94}Si_{1.59}K_{0.08}O_x]_1$).

The first 175 cm from top to bottom are thermostatted by means of a salt bath A pumped in countercurrent. The second 175 cm are thermostatted by means of a salt bath B pumped in countercurrent.

Second Reaction Stage:

A reaction tube (V2A steel; external diameter 30 mm, wall thickness 2 mm, internal diameter 26 mm, length: 350 cm, and also a thermal tube (external diameter 4 mm) centered in the middle of the reaction tube to receive a thermal element which can be used to determine the temperature in the reaction tube over its entire length) is charged from top to bottom as follows:

Section 1: length 20 cm steatite rings of geometry 7 mm×7 mm×4 mm (external diameter×length×internal diameter) as a preliminary bed.

Section 2: length 90 cm catalyst charge of a homogeneous mixture of 30% by weight of steatite rings of geometry 7 mm×3 mm×4 mm (external diameter×length×internal diameter) and 70% by weight of coated catalyst from section 4.

Section 3: length 50 cm catalyst charge of a homogeneous mixture of 20% by weight of steatite rings of geometry 7 mm×3 mm×4 mm (external diameter×length×internal diameter) and 80% by weight of coated catalyst from section 4.

Section 4: length 190 cm catalyst charge of annular (7 mm×3 mm×4 mm=external diameter×length×internal diameter) coated catalyst according to preparative example 5 of DE-A 10046928 (stoichiometry: $Mo_{12}V_3W_{1.2}Cu_{2.4}O_x$).

The first 175 cm from top to bottom are thermostatted by means of a salt bath C pumped in countercurrent. The second 175 cm are thermostatted by means of a salt bath D pumped in countercurrent.

Gas Phase Oxidation:

The above-described first reaction stage is continuously charged with a starting reaction gas mixture 1 of the following composition, and the loading and the thermostatting of the first reaction tube is varied:

from 6 to 6.5% by volume of propene,
from 3 to 3.5% by volume of $H_2O$,
from 0.3 to 0.5% by volume of CO,
from 0.8 to 1.2% by volume of $CO_2$,
from 0.01 to 0.04% by volume of acrolein,
from 10.4 to 10.7% by volume of $O_2$ and
the remainder ad 100% molecular nitrogen.

At the exit of the first reaction tube, a small sample is withdrawn from the product gas mixture of the first reaction stage for gas chromatography analysis. Otherwise, the product gas mixture is conducted directly into the subsequent acrolein oxidation stage (to acrylic acid) by jetting in air at a temperature of 25° C. (reaction stage 2).

A small sample is likewise taken from the product gas mixture of the acrolein oxidation stage for gas chromatography analysis. Otherwise, the acrylic acid is removed in a manner known per se from the product gas mixture of the second reaction stage and a portion of the remaining residual gas is reused for charging the propene oxidation stage (as cycle gas), which explains the acrolein content of the abovementioned charging gas and the low variance of the feed composition.

In both reaction stages, the reaction gas mixture flows through the two catalyst tubes from top to bottom.

The pressure at the entrance to the first reaction stage varies between 2.3 and 3.1 bar as a function of the propene hourly space velocity selected. At the end of the reaction zones A, C there is likewise an analysis point. The pressure at the entrance to the second reaction stage varies between 1.6 and 2.1 bar as a function of the acrolein hourly space velocity.

The results as a function of hourly space velocities and salt bath temperatures and also addition of air after the first reaction stage are shown by the following table (the letter E in brackets means example and the letter C in brackets means comparative example).

$T_A, T_B, T_C, T_D$ are the temperatures of the salt baths circulated by pumping in the reaction zones A, B, C and D in ° C.

$C_{PA}$ is the propene conversion at the end of reaction zone A in mol %.

$C_{PB}$ is the propene conversion at the end of reaction zone B in mol %.

$S_{WP}$ is the selectivity of acrolein formation and also of acrylic acid by-production taken together after the first reaction stage and based on converted propene in mol %.

$C_{AC}$ is the acrolein conversion at the end of reaction zone C in mol %.

$C_{AD}$ is the acrolein conversion at the end of reaction zone D in mol %

$C_{PD}$ is the propene conversion at the end of reaction zone D in mol % (based on the starting amount of propene in reaction zone A).

$S^{AA}$ is the selectivity of acrylic acid formation after the second reaction stage and based on converted propene in mol %.

R is the molar ratio of molecular oxygen:acrolein in the starting reaction gas mixture 2.

M is the amount of air added after the first reaction stage in l (STP)/h.

$T^{maxA}, T^{maxB}, T^{maxC}, T^{maxD}$ are each the highest temperature of the reaction gas mixture within the reaction zones A, B, C and D in ° C.

b) Results

TABLE

| Propene hourly space velocity (l(STP)/l · h) | $T_A$ | $T_B$ | $T^{maxA}$ | $T^{maxB}$ | $C_{PA}$ | $C_{PB}$ | $S_{WP}$ | M | R |
|---|---|---|---|---|---|---|---|---|---|
| 130 (E) | 319 | 319 | 384 | 351 | 66.7 | 95.1 | 97.7 | 404 | 1.40 |
| 130 (E) | 327 | 313 | 400 | 330 | 70.3 | 94.8 | 98.3 | 404 | 1.38 |
| 130 (C) | 311 | 325 | 361 | 372 | 60.8 | 95.0 | 97.1 | 404 | 1.41 |
| 185 (C) | 322 | 336 | 380 | 368 | 64.5 | 94.9 | 98.0 | 574 | 1.39 |
| 185 (C) | 310 | 344 | 353 | 383 | 57.2 | 95.2 | 97.3 | 574 | 1.40 |

| Acrolein hourly space velocity (l(STP)/l · h) | $T_C$ | $T_D$ | $T^{maxC}$ | $T^{maxD}$ | $C_{AC}$ | $C_{AD}$ | $C_{PD}$ | $S^{AA}$ |
|---|---|---|---|---|---|---|---|---|
| 160 (E) | 260 | 260 | 302 | 276 | 80.7 | 99.3 | 95.1 | 95.4 |
| 108 (E) | 262 | 259 | 312 | 275 | 84.8 | 99.3 | 94.8 | 95.8 |
| 104 (C) | 257 | 262 | 285 | 291 | 64.0 | 99.3 | 95.0 | 94.9 |
| 152 (C) | 263 | 269 | 303 | 287 | 78.8 | 99.3 | 94.9 | 95.8 |
| 147 (C) | 257 | 278 | 278 | 310 | 61.3 | 99.3 | 95.2 | 95.0 |

We claim:

1. A process for partially oxidizing propene to acrylic acid in the gas phase under heterogeneous catalysis by conducting a starting reaction gas mixture 1 which comprises propene, molecular oxygen and at least one inert gas, and contains the molecular oxygen and the propene in a molar $O_2:C_3H_6$ ratio of $\geq 1$ in a first reaction stage over a fixed catalyst bed 1 which is arranged in two spatially successive reaction zones A, B, the temperature of reaction zone A being a temperature in the range from 290 to 380° C. and the temperature of reaction zone B likewise being a temperature in the range from 290 to 380° C., and whose active composition is at least one multimetal oxide comprising the elements Mo, Fe and Bi, in such a way that reaction zone A extends to a propene conversion of from 40 to 80 mol % and the propene conversion on single pass through the fixed catalyst bed 1 is $\geq 90$ mol % and the accompanying selectivity of acrolein formation and also of acrylic acid by-production taken together is ≧90 mol %, the temperature of the product gas mixture leaving the first reaction stage is optionally reduced by cooling and molecular oxygen and/or inert gas are optionally added to the product gas mixture, and then the product gas mixture, as a starting reaction gas mixture 2 comprising acrolein, molecular oxygen and at least one inert gas and containing the molecular oxygen and the acrolein in a molar $O_2:C_3H_4O$ ratio of ≧0.5, is conducted in a second reaction stage over a fixed catalyst bed 2 which is arranged in two spatially successive reaction zones C, D, the temperature of reaction zone C being a temperature in the range from 230 to 320° C. and the temperature of reaction zone D likewise being a temperature in the range from 230 to 320° C., and whose active composition is at least one multimetal oxide comprising the elements Mo and V, in such a way that reaction zone C extends to an acrolein conversion of from 45 to 85 mol % and the acrolein conversion on single pass through the fixed catalyst bed 2 is ≧90 mol % and the selectivity of acrylic acid formation assessed over all reaction zones, based on converted propene, is ≧80 mol %, the sequence in time in which the reaction gas mixture flows through the reaction zones corresponding to the alphabetic sequence of the reaction zones, wherein a) the hourly space velocity of the propene contained in the starting reaction gas mixture 1 on the fixed catalyst bed 1 is <160 l (STP) of propene/l of fixed catalyst bed 1·h and ≧90 l (STP) of propene/l of fixed catalyst bed 1·h;

b) the volume-specific activity of the fixed catalyst bed 1 is either constant or increases at least once in the flow direction of the reaction gas mixture over the fixed bed catalyst bed 1;

c) the difference $T^{maxA}-T^{maxB}$, formed from the highest temperature $T^{maxA}$ which the reaction gas mixture has within reaction zone A and the highest temperature $T^{maxB}$ which the reaction gas mixture has within reaction zone B is ≧0° C.;

d) the hourly space velocity of the acrolein contained in the starting reaction gas mixture 2 on the fixed catalyst bed 2 is <145 l (STP) of acrolein/l of fixed catalyst bed 2·h and ≧70 l (STP) of acrolein/l of fixed catalyst bed 2·h;

e) the volume-specific activity of the fixed catalyst bed 2 increases at least once in the flow direction of the reaction gas mixture over the fixed bed catalyst bed 2; and f) the difference $T^{maxC}-T^{maxD}$ formed from the highest temperature TmaxC which the reaction gas mixture has within reaction zone C and the highest temperature $T^{maxD}$ which the reaction gas mixture has within reaction zone D, is ≧0° C.

2. A process as claimed in claim 1, wherein the difference $T^{maxA}-T^{maxB}$ is ≧3° C. and ≦70° C.

3. A process as claimed in claim 1, wherein the difference $T^{maxA}-T^{maxB}$ is ≧20° C. and ≦60° C.

4. A process as claimed in claim 1, wherein the difference $T^{maxC}-T^{maxD}$ is ≧3° C. and ≦60° C.

5. A process as claimed in claim 1, wherein the difference $T^{maxC}-T^{maxD}$ is ≧3° C. and ≦40° C.

6. A process as claimed in claim 1, wherein the hourly space velocity of the propene contained in the starting gas mixture on the fixed catalyst bed 1 is ≧100 l (STP) or propene/l·h and ≦150 l (STP) or propene/l·h.

7. A process as claimed in claim 1, wherein the hourly space velocity of the propene contained in the starting gas mixture on the fixed catalyst bed 1 is ≧110 l (STP) or propene/l·h and ≦145 l (STP) or propene/l·h.

8. A process as claimed in claim 1, wherein the difference $T_B-T_A$ between the temperature of reaction zone B, $T_B$, and the temperature of reaction zone A, $T_A$, is ≧−10° C. and ≦0° C.

9. A process as claimed in claim 1, wherein the difference $T_C-T_D$ between the temperature of reaction zone D, $T_D$, and the temperature of reaction zone C, $T_C$, is ≧−10° C. and ≦0° C.

10. A process as claimed in claim 1, wherein the temperature of reaction zone A is from 305 to 365° C.

11. A process as claimed in claim 1, wherein the temperature of reaction zone A is from 310 to 340° C.

12. A process as claimed in claim 1, wherein the temperature of reaction zone C is from 250 to 300° C.

13. A process as claimed in claim 1, wherein the temperature of reaction zone C is from 260 to 280° C.

14. A process as claimed in claim 1, wherein the active composition of the fixed catalyst bed 1 is at least one multimetal oxide active composition of the general formula I $$Mo_{12}Bi_aFe_bX^1_cX^2_dX^3_eX^4_fO_n \qquad (I)$$

where $X^1$=nickel and/or cobalt, $X^2$=thallium, an alkali metal and/or an alkaline earth metal, $X^3$=zinc, phosphorus, arsenic, boron, antimony, tin, cerium, lead and/or tungsten, $X^4$=silicon, aluminum, titanium and/or zirconium, a=from 0.5 to 5, b=from 0.01 to 5, c=from 0 to 10, d=from 0 to 2, e=from 0 to 8, f=from 0 to 10 and n=a number which is determined by the valency and frequency of the elements other than oxygen in I.

15. A process as claimed in claim 1, wherein the active composition of the fixed catalyst bed 2 is at least one multimetal oxide active composition of the general formula IV $$Mo_{12}V_aX^1_bX^2_cX^3_dX^4_eX^5_fX^6_gO_n \qquad (IV)$$

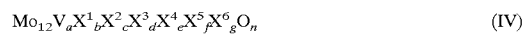

where the variables are defined as follows:

$X^1$=W, Nb, Ta, Cr and/or Ce, $X^2$=Cu, Ni, Go, Fe, Mn and/or Zn, $X^3$=Sb and/or Bi, $X^4$=one or more alkali metals, $X^5$=one or more alkaline earth metals, $X^6$=Si, Al, Ti and/or Zr, a=from 1 to 6, b=from 0.2 to 4, c=from 0.5 to 18, d=from 0 to 40, e=from 0 to 2, f=from 0 to 4, g=from 0 to 40 and n=a number which is determined by the valency and frequency of the elements other than oxygen in IV.

* * * * *